United States Patent [19]
Ketcham

[11] 4,093,359
[45] June 6, 1978

[54] OCULAR FIXATION AID

[76] Inventor: Ferris F. Ketcham, 4615 35th Ave., SW., Seattle, Wash. 98126

[21] Appl. No.: 725,968

[22] Filed: Sept. 23, 1976

[51] Int. Cl.² .......................... A61B 3/00; A61B 3/02
[52] U.S. Cl. .......................................... 351/1; 351/37
[58] Field of Search ................ 351/32, 37, 1; 46/123, 46/124, 138, 154

[56] References Cited

U.S. PATENT DOCUMENTS

| | | | |
|---|---|---|---|
| 2,326,225 | 10/1943 | Jeffrey | 46/137 |
| 2,453,646 | 11/1948 | Tomlin et al. | 46/123 |

*Primary Examiner*—Paul A. Sacher
*Assistant Examiner*—Rodney B. Bovernick

*Attorney, Agent, or Firm*—Christensen, O'Connor, Johnson & Kindness

[57] ABSTRACT

To attract and maintain the gaze of a patient's eyes (particularly those of a child) during an ophthalmalic examination, a small animatable fixation target, such as a toy animal having movable body parts, is mounted on one end of a support, and the other end of the support is held in the mouth of the physician who is conducting the examination. The support includes means for animating the target in reaction to pressure of the teeth on the orally held support, so that the physician can control movement of the target for fixing the patient's gaze and for stimulating accommodation of the patient's eyes while freeing the physician's hands for holding other instruments needed during the examination.

5 Claims, 3 Drawing Figures

OCULAR FIXATION AID

BACKGROUND OF THE INVENTION

The invention pertains to ocular fixation aids for use by ophthalmologists, physicians and other medical personnel when examining and treating a patient's eyes, and particularly to ocular fixation aids that are effective to attract and maintain the patient's gaze and to stimulate accommodation (focusing of the eyes).

Ocular fixation aids are in general known and have been found especially useful when examining the eyes of infants and young children. Because infants and children have difficulty in following instructions and in maintaining visual concentration, such aids are used to display a small visually interesting object, called a target, to the patient that spontaneously attracts and thereafter holds the patient's gaze fixed on the object while the examination is carried out. An example of a known ocular fixation aid is disclosed in U.S. Pat. No. 3,484,155 issued to D. L. Prager et al.

However, known fixation aids have exhibited certain limitations which detract from their effectiveness. For example, the aid disclosed in U.S. Pat. No. 3,484,155 is mounted on a head strap worn by the person conducting the examination, and is thus not capable of being used concurrently with other types of head strap mounted instruments employed during ocular examinations. Furthermore, the fixation targets provided in U.S. Pat. No. 3,484,155 (two are disclosed) are inanimate, and as such, are not effective to maintain the patient's attention for more than brief periods. One target is a stationary toy figure. The other target is a toy figure supporting a small light connected to a blinking circuit that when turned on by a manually operated switch, blinks on and off at a constant rate. The constant repetition of the blinking light will soon result in disinterest of the patient. The repetition of the blinking light may be varied by turning the manually operated switch on and off however, such requires the use of one of the hands of the person conducting the examination, a hand that may be needed for holding another instrument or implement, such as an occluder.

It is therefore an object of the present invention to provide an entirely new approach to the design of such devices, an approach that is not subject to the foregoing limitations.

In particular it is an object of the present invention to provide an ocular fixation aid that can be held and oriented by the person conducting the examination in a way that does not interfere with the use of such person's hands for other purposes associated with the examination, and also does not interfere with the use of the various types of head mounted instruments that are available for assisting in the examination of eyes and treatment of ocular abnormalities.

Another object of the present invention is to provide an ocular fixation aid in which the target can be animated at will by the person conducting the examination so as to maintain the interest of the patient, and in which the animation of the target can be effected without requiring the use of such person's hands. A related object is to enable the person that is conducting the examination to control the timing of the target animation so that he can more readily observe accomodation of the patient's eyes as they focus on the movement of the target.

A further object of the present invention is to provide an ocular fixation aid that satisfies the above objectives and that is of relatively simple construction, that is readily mass produced at a low per unit cost, and that is durable and relatively small so that, for example, it can be carried in a physician's coat pocket, ready for use.

SUMMARY OF THE INVENTION

To achieve these objects the present invention provides an orally held ocular fixation aid to be used during the examination or treatment of a patient's eyes, in which the fixation aid includes an animatable means, such as a toy animal having movable body parts, that when animated present an eye-attracting fixation target. The animatable means is mounted on one end of a support. The other end of the support is sized and shaped so that it can be held in the mouth and gripped between the teeth of the person conducting the examination. When so held, the end of the support that mounts the animatable means projects from the mouth and orients the animatable means at a desired position. Means are associated with the support for animating the animatable means in reaction to pressure of the teeth on the support. Thus, the person conducting the examination can orient the support and the animatable means at a desired position with respect to his vision and can produce movement of the animatable means by varying the pressure by which his teeth grip the support.

In a preferred form of the invention, the support is provided by a pair of elongate superposed members. One set of ends of the members (corresponding to the orally held end of the support) are articulated to enable relative movement of the opposite set of member ends between a spaced relationship and a closed relationship. Means are provided for biasing the members to cause their non-articulated ends to normally assume the spaced relationship, such that when the support is orally held, an increasing gripping pressure on the support forces the non-articulated ends toward the closed relationship, against the bias. The animatable means is mounted on at least one of the members and is animated in reaction to movement of the non-articulated ends between the spaced and closed relationships.

Preferably the elongate members that form the support are of generally flat shape and are arranged face-to-face. The articulated ends are rounded so as to be suitable for being orally held and are joined by an elastomeric member insert sandwiched between the mutually opposed surfaces of the two members and secured in place therebetween. The elasticity of the insert affords a hinge-like articulation of the members enabling the abovementioned relative movement between the non-articulated ends. Preferably, the animatable means is provided by a toy, such as a toy animal, of the type in which the body of the toy is formed by a plurality of apertured segments that are strung together by one or more threads and in which the toy is animated by varying the tension in the threads.

It is thus seen that the ocular fixation aid provided in accordance with the present invention is adapted to be orally held by the person who is conducting the examination. When so held the animatable means that defines the target can be oriented at a desired position with respect to the line of vision of the person who is conducting the examination. As required to attract and hold the patient's gaze or to stimulate accommodation, the animatable means is animated by varying the pressure exerted by the teeth on the orally held support. The fixation aid in its preferred form is relatively small and is durable and is thus suitable for being carried in a coat pocket, ready for use.

To provide a complete disclosure of the invention, reference is made to the appended drawings and following description of one particular and preferred embodiment.

DESCRIPTION OF THE PREFERRED EMBODIMENT

Figure 1:
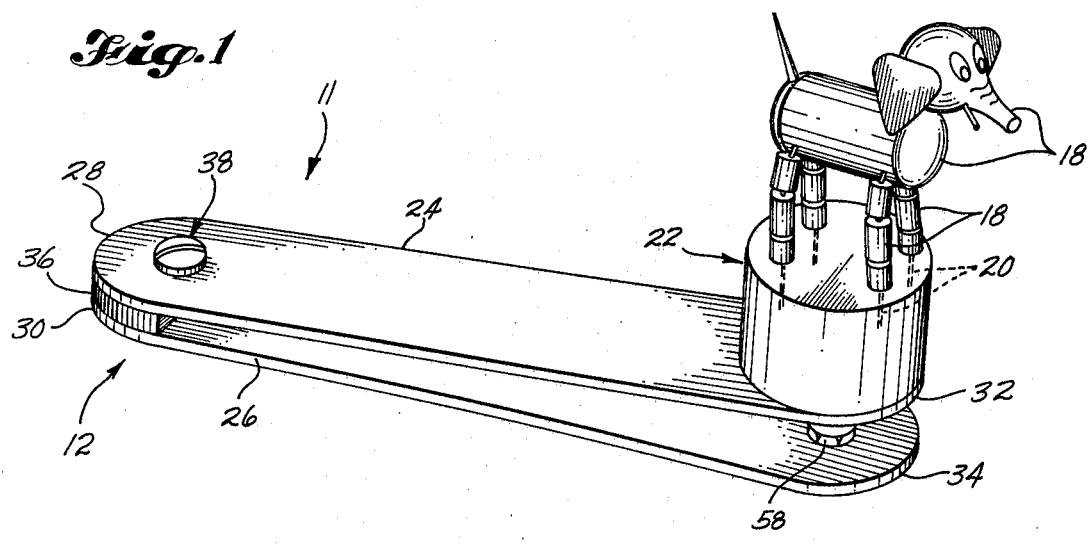
FIG. 1 is an isometric view of the preferred embodiment of the ocular fixation aid.

With reference to FIG. 1, the ocular fixation aid in its preferred form includes an elongate support 11 having a first end 12 and a second end 14. The first end 12 is sized and shaped so as to be suitable for being held in the mouth of the person conducting the examination and the second end 14 has an animatable toy 16 mounted thereon. Toy 16, having a body of an animal or other object formed by a plurality of disjointed, apertured segments strung on threads 20, is animatable as described more fully herein.

Support 11 is formed of elongate, relatively flat, generally parallel, upper and lower members 24 and 26 arranged face-to-face with ends 28 and 30, respectively, coterminating at a first end 12 of support 11, and ends 32 and 34, respectively, coterminating at the second end 14 of support 11. Ends 28 and 30 are rounded as shown in FIG. 1 inasmuch as end 12 is intended to be inserted in the mouth and should be free of corners or sharp edges that might cause discomfort to the user. Although members 24 and 26 may be made of any number of materials such as plastic or metal, I have found that wood is the most satisfactory material because of its stiffness and lightness of weight, and because wood is not uncomfortable to hold in the mouth and grip between the teeth.

Members 24 and 26 are connected together at end 12 by an articulated joint that includes a semicircular, wafer-like elastomeric member 36 sandwiched between the confronting faces of members 24 and 26 adjacent ends 28 and 30. A belt screw 38 having an externally threaded shank 38a and an internally threaded nut-like part 38b extends through aligned bores in members 24 and 26, transversely oriented to members 24 and 26. When assembled and tightened, belt screw 38 clamps elastomeric member 36 between the confronting faces of members 24 and 26 adjacent end 12. The securement of the joint may be augmented by the application of an adhesive to those opposed faces of elastomeric member 36 which contact the confronting faces of members 24 and 26. The elastic compressibility of member 36 permits members 24 and 26 to articulate about a pivot located at belt screw 38 thereby permitting relative movement between ends 32 and 34.

It is the relative movement between ends 32 and 34 that animates toy 16. In particular, toy 16 includes a base assembly 22 having a hollow cylindrical base 42 closed by an upper end wall 44 to provide a platform for the body segments 18 of the toy. The lower and open end 46 of base 42 is supportively secured to an upper face of member 24 adjacent end 32. A cup shaped plunger 48 is mounted for coaxial reciprocation within base 42 and a helical compression spring 50 is coaxially disposed within base 42 and acts between plunger 48 and the interior of end wall 44 of base 42 to bias plunger 48 downwardly away from end wall 44. Threads 20 of toy 16 pass through apertures provided in end wall 44 and extend downwardly therefrom to plunger 48 to which they are secured. The bias of spring 50 urges plunger 48 downwardly so as to tension threads 20 and thereby maintain toy 16 in a normally erect posture. To animate the toy 16, plunger 48 is displaced upwardly to slacken threads 20 and thereby cause the toy to collapse. For this purpose, a flat head machine screw 52 is passed upwardly through a countersunk bore provided in lower member 26 adjacent it end 34 with the head screw 54 being disposed flush with the lower surface of member 26. The upper threaded end of screw 52 is threaded into a self-threading bore 56 provided in plunger 48. A nut 58 threaded onto the shank of screw 52 beforehand, is tightened against the upper surface of member 26 to secure screw 52 to the lower member 26.

Figure 2:
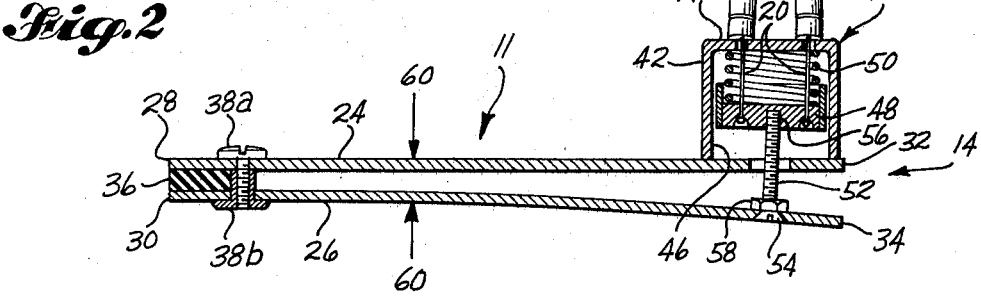
FIG. 2 is a longitudinal and vertical sectional view of the fixation aid shown in FIG. 1, in which part of the animatable toy shown in FIG. 1 is omitted in this view.

The various parts of support 11 and base assembly 22 are dimensioned and assembled so that spring 50 urges plunger 48 away from end wall 44 of base 42 to bias ends 32 and 34 of members 24 and 26 in a spread apart relationship, as shown in FIG. 2, and to pull threads 20 taut so that toy 16 is held erect. In response to a compressive force 60 applied to the upper and lower surfaces of members 24 and 26, such as by the gripping pressure of teeth, members 24 and 26 are forced toward each other at ends 32 and 34. This forces screw 52 upwardly causing plunger 48 to be upwardly depressed into base 42. Threads 20 are thus slackened, and toy 16 collapses.

Figure 3:
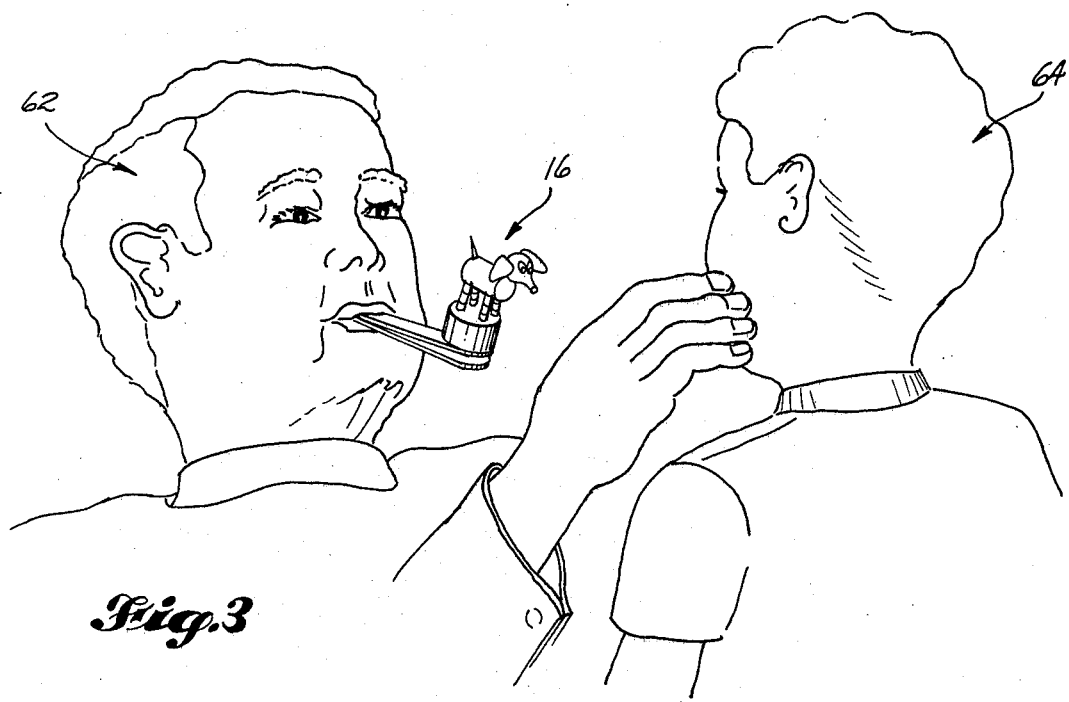
FIG. 3 is a perspective view showing the use of the ocular fixation aid by an ophthalmologist conducting an examination of a child's eyes.

With reference to FIG. 3, support 11 of the ocular fixation aid is held in the mouth of the ophthalmologist 62 and oriented relative to his forward line of vision so that toy 16 is at a desired position for fixing the gaze of the patient 64. The ophthalmologist grips members 24 and 26 of support 11 between his teeth and increases the gripping pressure until plunger 48 is depressed into base 42 causing the toy to collapse. The gripping pressure is released to cause the toy to return to the erect posture. Variable gripping pressure on support 11 animates the toy between erect and collapsed postures as needed to produce the desired ocular response of the patient, such as accommodation when a child's eyes are being examined, it is desirable to frequently animate toy 16 to attract and maintain the attention of the child.

While only a particular embodiment of the invention has been disclosed herein it will be readily apparent to persons skilled in the art that numerous changes and modifications can be made thereto without departing from the principles of the invention.

What is claimed is:

1. An orally held ocular fixation aid for use during the examination of a patient's eyes comprising:
   animatable means for providing a fixation target that is effective when animated to attract and maintain the gaze of a patient and to stimulate accommodation;
   a support means having a first end and a second end, said first end being sized and shaped for being held in the mouth of a person conducting the examination and for being gripped between such person's teeth, said second end projecting from the mouth of such person when the first end is so held, said animatable means being mounted on said support means adjacent said second end; and means associated with said support means for animating said animatable means in response to a change in pressure of the grip exerted by the teeth of such person.

2. The ocular fixation aid of claim 1, wherein said support means comprises:

a pair of elongate members disposed generally parallel to each other and having a first set of generally coterminous ends that define said first end and a second set of generally coterminous ends that define said second end, means connecting said first set of ends for articulation so that said second set of ends are movable from a spaced relationship toward a closed relationship, and vice versa;

means for biasing said members so that said second set of ends assume said spaced relationship and are responsive to an increase in pressure exerted by the teeth of a person when holding said support means in such person's mouth to move toward said closed relationship;

said animatable means being mounted on at least one of said members; and said means for animating said animatable means including means responsive to movement of said second set of ends between said spaced relationship and said closed relationship.

3. The ocular fixation aid of claim 1, wherein said animatable means comprises: a body, said body being formed of a plurality of apertured, disjointed segments; thread means threading apertures of said segments; and wherein said means for animating said animatable means comprises means for alternately tensioning and slackening said thread means so as to cause said body to alternately assume erect and collapsed postures, respectively.

4. The ocular fixation aid of claim 2, wherein said means connecting said first set of coterminous ends comprises an elastomeric member secured between mutually opposed surface portions of said members adjacent said first set of coterminous ends.

5. The ocular fixation aid of claim 3, wherein said means connecting said first set of coterminous ends comprises an elastomeric member secured between mutually opposed surface portions of said members adjacent said first set of coterminous ends.

* * * * *